(12) United States Patent
Shrivastava et al.

(10) Patent No.: US 9,597,171 B2
(45) Date of Patent: Mar. 21, 2017

(54) RETRIEVAL CATHETER WITH EXPANDABLE TIP

(75) Inventors: Sanjay Shrivastava, Irvine, CA (US); Wenfeng Lu, Irvine, CA (US); Anh Cam, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 488 days.

(21) Appl. No.: 13/609,777

(22) Filed: Sep. 11, 2012
(Under 37 CFR 1.47)

(65) Prior Publication Data
US 2014/0074144 A1 Mar. 13, 2014

(51) Int. Cl.
*A61F 11/00* (2006.01)
*A61F 2/01* (2006.01)
(Continued)

(52) U.S. Cl.
CPC .............. *A61F 2/01* (2013.01); *A61B 17/221* (2013.01); *A61B 17/22031* (2013.01);
(Continued)

(58) Field of Classification Search
CPC ........ A61B 17/12022; A61B 17/22031; A61B 17/22032; A61B 17/221; A61B 2017/00557; A61B 2017/2215; A61B 2017/22051; A61B 17/1204; A61B 17/12109; A61B 17/12131; A61B 17/12172; A61B 17/12136; A61B 1/32; A61B 17/02; A61B 17/0206; A61B 17/0218; A61B 17/0231; A61B 17/025; A61B 17/0281; A61B 17/0293; A61B 2017/0212; A61B 2017/0225; A61B 2017/0237; A61B 2017/0243; A61B 2017/0256; A61B 2017/0262; A61B 2017/0268; A61B 2017/0275; A61B 2017/0287; A61M 25/0067; A61M 25/0068; A61M 25/0069; A61M 25/007; A61M 25/0071; A61M 25/0074; A61M 25/0075;
(Continued)

(56) References Cited

U.S. PATENT DOCUMENTS 3,831,587 A 8/1974 Boyd
3,896,815 A * 7/1975 Fettel et al. .................. 606/194
(Continued)

FOREIGN PATENT DOCUMENTS

EP 2158858 A1 3/2010
WO WO-84/01513 A1 4/1984
(Continued)

OTHER PUBLICATIONS

U.S. Appl. No. 14/056,461, filed Oct. 17, 2013.

*Primary Examiner* — Jonathan Miles
*Assistant Examiner* — Kankindi Rwego
(74) *Attorney, Agent, or Firm* — Mark J. Kertz, Esq.

(57) ABSTRACT

Catheters of the present disclosure include a catheter shaft and an expandable tip, which can retrieve materials slightly larger than an inner diameter of the catheter shaft. The tip may be expandable such that it can easily transform from a first size and shape to a second size and shape to aid in the retrieval of the materials (i.e., the thrombus, embolus, or foreign body). Catheter tips may be expanded by inflation, removal of a constraining member, or an input such as heat, light, or electrical energy.

19 Claims, 7 Drawing Sheets

(51) Int. Cl.
*A61B 17/22* (2006.01)
*A61B 17/221* (2006.01)
*A61M 25/10* (2013.01)
*A61B 17/00* (2006.01)
*A61B 17/12* (2006.01)

(52) U.S. Cl.
CPC .............. *A61B 17/22032* (2013.01); *A61B 2017/00287* (2013.01); *A61B 2017/00557* (2013.01); *A61B 2017/12059* (2013.01); *A61B 2017/2215* (2013.01); *A61B 2017/22034* (2013.01); *A61M 25/1002* (2013.01); *A61M 2025/109* (2013.01)

(58) Field of Classification Search
CPC ............ A61M 25/008; A61M 25/0082; A61M 2025/0024; A61M 2025/0073; A61M 2025/0076; A61M 2025/0078; A61M 2025/0079; A61M 2025/0081; A61M 2025/109
USPC ....... 606/108, 127, 159, 191, 192, 194, 200; 604/19, 48, 96.01, 97.01
See application file for complete search history.

(56) References Cited

U.S. PATENT DOCUMENTS

| | | | |
|---|---|---|---|
| 4,611,594 | A | 9/1986 | Grayhack et al. |
| 5,011,488 | A | 4/1991 | Ginsburg |
| 5,102,415 | A | 4/1992 | Guenther et al. |
| 5,308,356 | A * | 5/1994 | Blackshear, Jr. ... A61M 25/1002 604/101.01 |
| 5,549,626 | A | 8/1996 | Miller et al. |
| 5,713,853 | A | 2/1998 | Clark et al. |
| 5,846,251 | A | 12/1998 | Hart |
| 5,868,753 | A * | 2/1999 | Schatz ............ 606/108 |
| 5,908,435 | A * | 6/1999 | Samuels ........... 606/200 |
| 5,971,938 | A | 10/1999 | Hart et al. |
| 6,139,517 | A * | 10/2000 | Macoviak ...... A61M 25/1002 604/101.05 |
| 6,245,088 | B1 | 6/2001 | Lowery |
| 6,277,136 | B1 * | 8/2001 | Bonutti ............ A61B 17/3439 600/204 |
| 6,605,102 | B1 | 8/2003 | Mazzocchi et al. |
| 6,626,861 | B1 | 9/2003 | Hart et al. |
| 6,638,293 | B1 | 10/2003 | Makower et al. |
| 6,663,650 | B2 | 12/2003 | Sepetka et al. |
| 6,682,505 | B2 * | 1/2004 | Bates .............. A61B 17/22 604/103.07 |
| 6,682,543 | B2 | 1/2004 | Barbut et al. |
| 6,702,830 | B1 | 3/2004 | Demarais et al. |
| 6,824,545 | B2 | 11/2004 | Sepetka et al. |
| 7,285,126 | B2 | 10/2007 | Sepetka et al. |
| 7,300,429 | B2 | 11/2007 | Fitzgerald et al. |
| 7,399,308 | B2 | 7/2008 | Borillo et al. |
| 7,727,242 | B2 | 6/2010 | Sepetka et al. |
| 7,766,921 | B2 | 8/2010 | Sepetka et al. |
| 7,837,702 | B2 | 11/2010 | Bates |
| 7,846,175 | B2 | 12/2010 | Bonnette et al. |
| 8,075,510 | B2 * | 12/2011 | Aklog ............ A61B 17/22 604/103.07 |
| 8,252,017 | B2 | 8/2012 | Paul, Jr. et al. |
| 8,298,257 | B2 | 10/2012 | Sepetka et al. |
| 8,343,170 | B2 | 1/2013 | Massicotte et al. |
| 8,784,441 | B2 | 7/2014 | Rosenbluth et al. |
| 8,795,305 | B2 | 8/2014 | Martin et al. |
| 2001/0037126 | A1 | 11/2001 | Stack et al. |
| 2003/0163158 | A1 | 8/2003 | White |
| 2005/0085826 | A1 | 4/2005 | Nair et al. |
| 2005/0159770 | A1 | 7/2005 | Divani et al. |
| 2005/0187570 | A1 | 8/2005 | Nguyen et al. |
| 2006/0135962 | A1 * | 6/2006 | Kick ............... A61B 17/3478 606/108 |
| 2006/0282116 | A1 | 12/2006 | Lowe et al. |
| 2007/0027520 | A1 | 2/2007 | Sherburne |
| 2008/0058836 | A1 | 3/2008 | Moll et al. |
| 2009/0043330 | A1 | 2/2009 | To |
| 2009/0054918 | A1 | 2/2009 | Henson |
| 2010/0030256 | A1 | 2/2010 | Dubrul et al. |
| 2010/0191272 | A1 | 7/2010 | Keating |
| 2010/0211156 | A1 | 8/2010 | Linder et al. |
| 2011/0077680 | A1 | 3/2011 | Heuser |
| 2011/0160762 | A1 | 6/2011 | Hogendijk et al. |
| 2011/0213290 | A1 | 9/2011 | Chin et al. |
| 2011/0218560 | A1 | 9/2011 | Ramzipoor et al. |
| 2011/0288529 | A1 | 11/2011 | Fulton |
| 2012/0143239 | A1 * | 6/2012 | Aklog ............ A61B 17/3207 606/200 |
| 2013/0102996 | A1 | 4/2013 | Strauss |
| 2013/0253569 | A1 | 9/2013 | Sepetka et al. |
| 2014/0277013 | A1 | 9/2014 | Sepetka et al. |

FOREIGN PATENT DOCUMENTS

| | | |
|---|---|---|
| WO | WO-92/18195 A1 | 10/1992 |
| WO | WO-2008/021013 A1 | 2/2008 |
| WO | WO-2009/120761 A1 | 10/2009 |
| WO | WO-2010/001405 A1 | 1/2010 |
| WO | WO-2012/009675 | 1/2012 |

\* cited by examiner

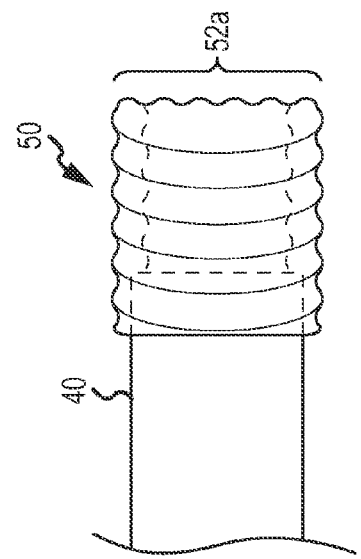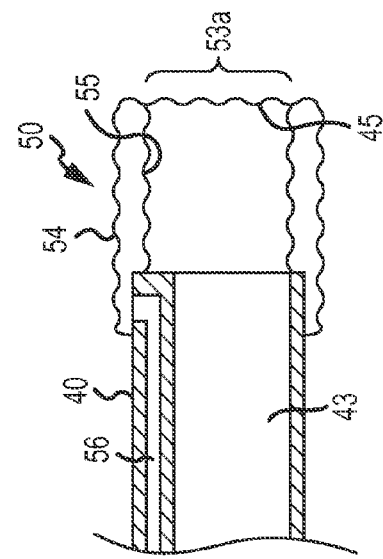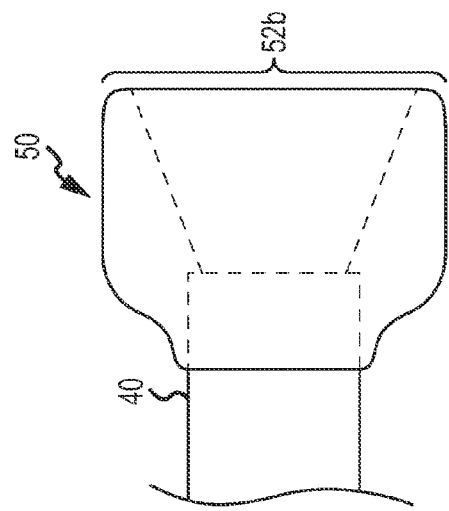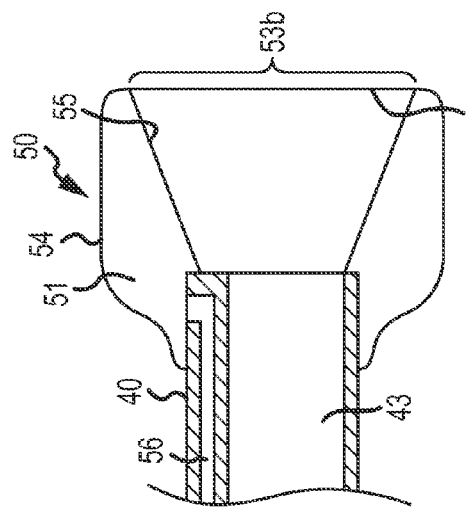
FIG. 2
FIG. 4
FIG. 3
FIG. 5

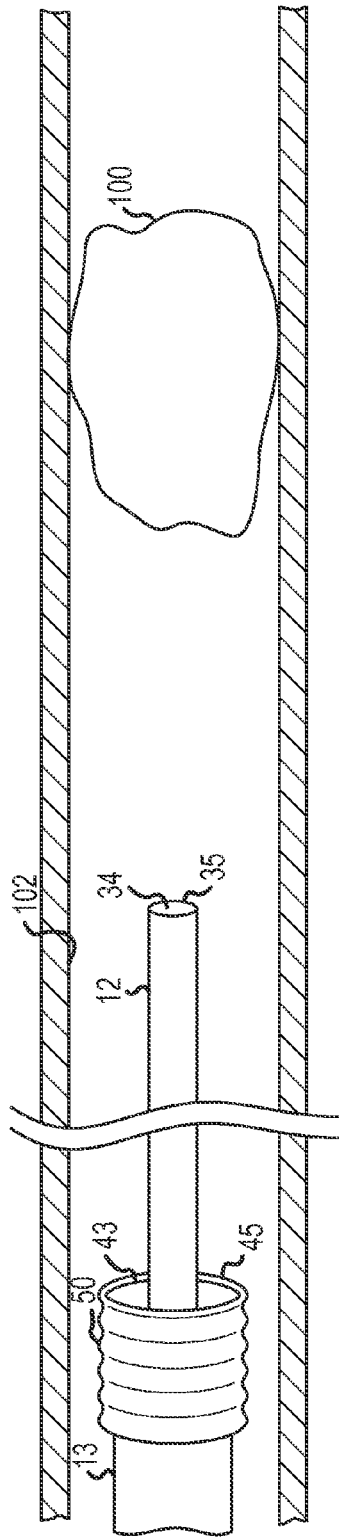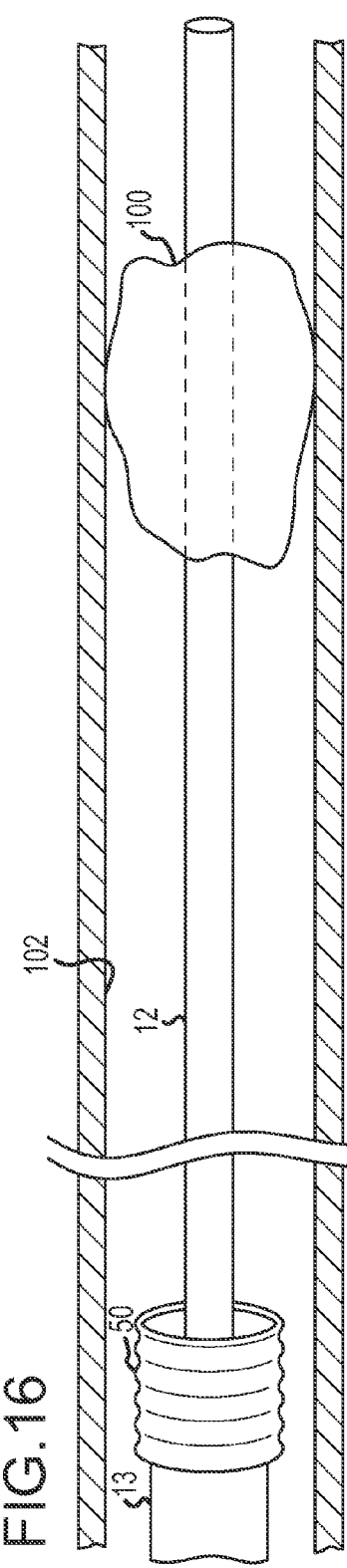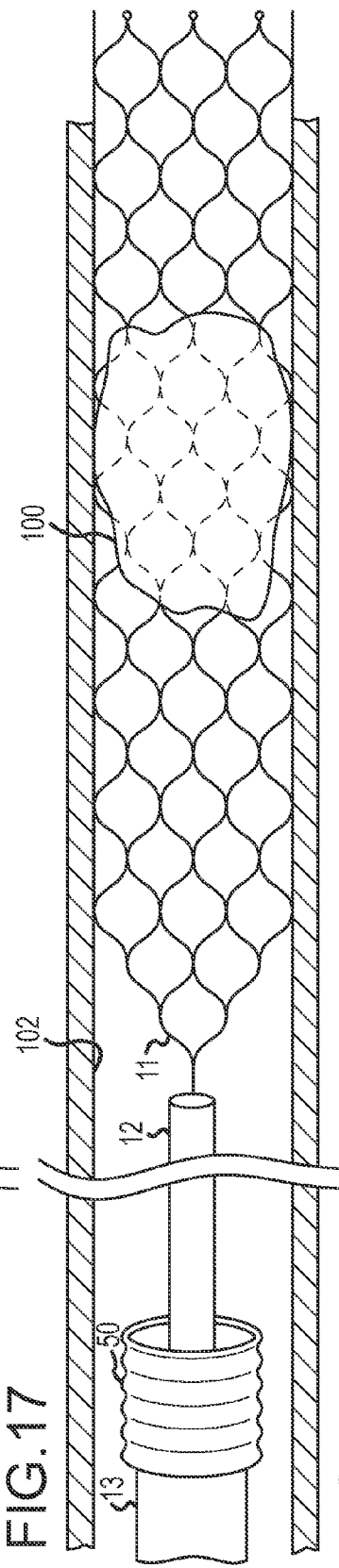

RETRIEVAL CATHETER WITH EXPANDABLE TIP

BACKGROUND

Removal of foreign bodies or thrombi using retrieval devices is often practiced during surgical endovascular procedures. In endovascular procedures, the process entails positioning of a guide catheter within a blood vessel. A retrieval device is introduced through the guide catheter and navigated toward the foreign body or lesion of interest in the vessel. The retrieval device is retrieved through the guide catheter once the foreign body or thrombus is captured.

SUMMARY

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

1. A retrieval catheter, comprising:
   an elongate shaft having a shaft lumen extending from a proximal end portion to a distal end portion of the elongate shaft;
   an inflatable tip disposed at a distal end of the elongate shaft, the inflatable tip extending distally of the distal end and forming a tip lumen distally of the distal end;
   wherein, in a first, unexpanded state, the tip lumen has a first cross-sectional dimension;
   wherein, in a second, expanded state, the tip lumen has a second cross-sectional dimension greater than the first cross-sectional dimension.

2. The catheter of clause 1, wherein, in the first state, the inflatable tip has a cylindrical profile.

3. The catheter of clause 1, wherein, in the second state, the inflatable tip has a frusticonical profile.

4. The catheter of clause 1, wherein the inflatable tip comprises a radially outer surface and a radially inner surface more compliant than the radially outer surface.

5. The catheter of clause 1, wherein, in the second state, the inflatable tip has a greater volume than in the first state.

6. The catheter of clause 1, wherein in the first state, the inflatable tip has a first outer cross-sectional dimension and wherein, in the second state, the inflatable tip has a second outer cross-sectional dimension greater than the first outer cross-sectional dimension;

7. The catheter of clause 1, wherein the inflatable tip is in fluid communication with a fluid source.

8. The catheter of clause 7, further comprising a pump configured to controllably move fluid between the inflatable tip and the fluid source.

9. The catheter of clause 1, wherein the inflatable tip comprises a pathway from a proximal end of the inflatable tip to the distal end of the inflatable tip.

10. The catheter of clause 9, wherein the pathway forms a spiral.

11. The catheter of clause 1, wherein the inflatable tip extends a greater longitudinal distance in the second state than in the first state.

12. A method of treating a blood vessel, comprising:
    advancing an elongate shaft within the vessel to a location adjacent an object within the vessel, the elongate shaft having a shaft lumen extending from a proximal end portion to a distal end portion of the elongate shaft;
    inflating an inflatable tip disposed at a distal end of the elongate shaft and extending distally of the distal end to form a tip lumen distally of the distal end, whereby the inflatable tip transitions from a first, unexpanded state, wherein the tip lumen has a first cross-sectional dimension, to a second, expanded state, wherein the tip lumen has a second cross-sectional dimension greater than the first cross-sectional dimension; and
    receiving the object into the shaft lumen through the tip lumen.

13. The method of clause 12, wherein inflating the inflatable tip comprises moving fluid from a fluid source to an interior region of the inflatable tip.

14. The method of clause 12, whereby an inner radial surface and an outer radial surface of the inflatable tip expand radially outward.

15. The method of clause 12, wherein receiving the object comprises providing suction at the distal end of the elongate shaft.

16. A retrieval catheter, comprising:
    an elongate shaft having a shaft lumen extending from a proximal end portion to a distal end portion of the elongate shaft, the elongate shaft having a distal end comprising a self-expanding member that expands from a collapsed state to an expanded state when unrestrained, the member extending distally of the distal end and forming a tip lumen distally of the distal end;
    a cover over an outer surface of the self-expanding member that retains the member in the collapsed state, the cover being at least partially dissolvable when activated, wherein the self-expanding member is configured to expand to the expanded state when the cover is at least partially dissolved.

17. The retrieval catheter of clause 16, wherein the self-expanding member comprises a plurality of woven strands.

18. The retrieval catheter of clause 16, wherein the self-expanding member comprises a spiral coil.

19. The retrieval catheter of clause 16, wherein the self-expanding member is substantially cylindrical in the first state.

20. The retrieval catheter of clause 16, wherein the self-expanding member is substantially frusticonical in the second state.

21. The retrieval catheter of clause 16, wherein the self-expanding member comprises a plurality of longitudinal slits.

22. The retrieval catheter of clause 16, wherein the cover is water-soluble.

23. The retrieval catheter of clause 16, wherein the cover is dissolvable when activated by an electric voltage.

24. The retrieval catheter of clause 16, wherein the cover is dissolvable when activated by light.

25. The retrieval catheter of clause 16, wherein the cover is dissolvable when activated by heat.

26. A method of treating a blood vessel, comprising
    advancing an elongate shaft within the vessel to a location proximal to an object within the vessel, the elongate shaft having (i) a shaft lumen extending from a proximal end portion to a distal end portion of the elongate shaft and (ii) a distal end comprising a self-expanding member that forms a tip lumen distally of the distal end and that expands from a collapsed state to an expanded state when unrestrained;

dissolving a cover positioned over and restrains the self-expanding member from expanding, whereby the self-expanding member transitions from the collapsed state having a first tip lumen cross-sectional dimension to the expanded state having a second tip lumen cross-sectional dimension greater than the first cross-sectional dimension; and receiving the object into the shaft lumen through the tip lumen.

27. The method of clause 26, wherein dissolving the cover comprises exposing the cover to blood.

28. The method of clause 26, wherein dissolving the cover comprises exposing the cover to one or more of a voltage, light, or heat.

29. The method of clause 26, wherein receiving the object comprises providing suction at the distal end of the elongate shaft.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 2, 3, 4, and 5 show an exemplary inflatable tip of a retrieval catheter tip, according to embodiments of the present disclosure.

FIG. 16 shows a step of an exemplary method, wherein a retrieval catheter approaches a thrombus, according to embodiments of the present disclosure.

FIG. 17 shows a step of an exemplary method, wherein a retrieval catheter crosses a thrombus, according to embodiments of the present disclosure.

FIG. 18 shows a step of an exemplary method, wherein a retrieval device engages a thrombus, according to embodiments of the present disclosure.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Retaining a captured foreign body or thrombus within a retrieval device is a goal of thrombectomy devices and methods, particularly as the device is withdrawn from the vessel into a guide catheter. The narrower diameter of the guide catheter relative to the vessel creates difficulty in retaining the captured foreign body or thrombus within the retrieval device. The process may even be hazardous because the captured foreign body or thrombus can break away and result in occlusion of blood vessels.

According to embodiments, catheters of the present disclosure include a catheter shaft and an expandable tip, which can retrieve materials larger than an inner diameter of the catheter shaft. The distal catheter tip may be expandable such that it can easily transform from a first size and shape to a second size and shape to aid in the retrieval of the materials (i.e., the thrombus, embolus, or foreign body). Such expansion capabilities may define a pathway for effective capture and removal of a thrombus or other materials. Such a pathway may increase the amount of material that is successfully removed from the vasculature, which thereby decreases the risk that such materials will escape and embolize.

Figure 1:
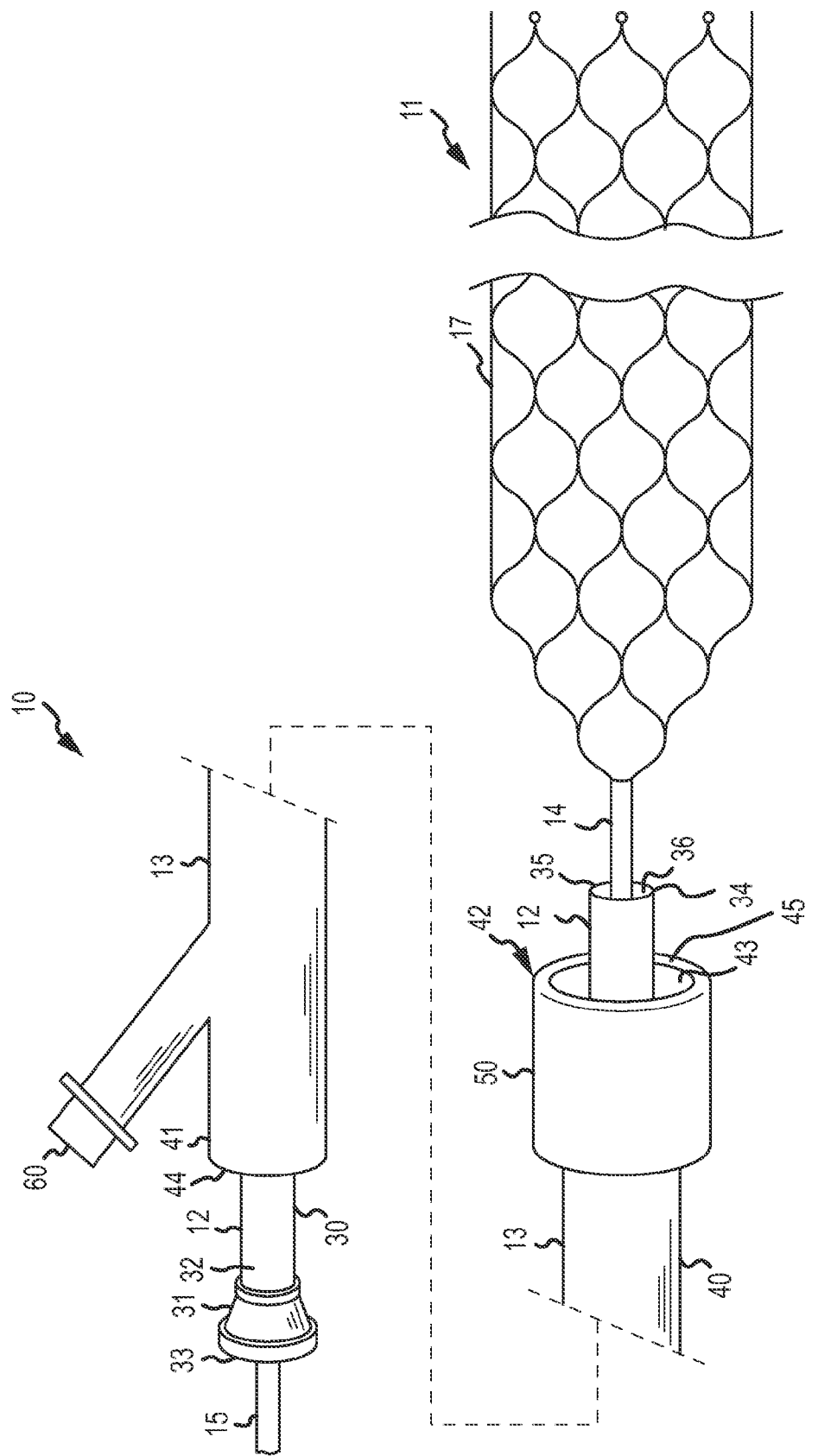
FIG. 1 shows an exemplary retrieval system, according to embodiments of the present disclosure.

FIG. 1 schematically illustrates an intracorporeal retrieval system 10 having features according to exemplary embodiments of the present disclosure. Retrieval system 10 depicted includes retrieval device 11, delivery catheter 12, and guide or retrieval catheter 13. In some instances only retrieval device 11 and either delivery catheter 12 or guide catheter 13 are required.

According to some embodiments, retrieval device 11 may be a device configured to act upon a thrombus, embolus, clot, occlusion, debris, foreign body or other mass within a blood vessel. Retrieval device 11 may include any device configured to engage, transport, treat, modify, or alter a mass. Commercially available devices which may be suitable for use as retrieval devices include the SOLITAIRE FR™ Revascularization Device, which is available from ev3, Inc., and the ALLIGATOR™ Retrieval Device. Incorporated herein by reference are U.S. Pub. No. 2011/0060212, published on Mar. 10, 2011; U.S. Pub. No. 2010/0331853, published on Dec. 30, 2010; and U.S. Pat. No. 6,679,893, issued on Jan. 20, 2004.

According to some embodiments, as shown in FIG. 1, delivery catheter 12 may include tubular body 30 with adapter 31 on proximal end 32, port 33 in adapter 31, distal end 34, port 35 in distal end 34 and inner lumen 36 extending between and in fluid communication with proximal port 33 and distal port 35. Inner lumen 36 is configured to receive slidably the retrieval device 11 with engaging portion 17 in a radially-reduced configuration. Adapter 31 is preferably provided with a hemostatic valve (not shown).

According to some embodiments, delivery catheter 12 is generally constructed to track over a conventional guidewire beyond the guide catheter 13 in the cervical anatomy and into the cerebral vessels associated with the brain and may also be chosen according to several standard, "microcatheter" designs that are generally available. Accordingly, delivery catheter 12 has a length that is at least 125 cm long, and more particularly may be between about 125 cm and about 175 cm long. Typically the delivery catheter 12 is about 155 cm long. Inner lumen 36 of the delivery catheter generally has an inner diameter between about 0.01 inch and about 0.098 inch (0.25-2.49 mm). Other designs and dimensions are contemplated. Commercially available microcatheters which may be suitable for use as delivery catheters include the REBAR™ Reinforced Micro Catheter, which is available from ev3, Inc., the MARKSMAN™ Catheter, which is available from ev3, Inc., the TURBOTRAKER™ catheter, which is available from Target Therapeutics, Inc., and the RAPIDTRANSIT™ catheter available from Cordis Endovascular Corporation.

According to some embodiments, also shown in FIG. 1 is guide catheter 13 having elongate body 40, proximal end 41, distal end 42, and inner lumen 43 extending between proximal port 44 and distal port 45 of guide catheter 13. Proximal end 41 of guide catheter 13 may be provided with an adapter (not shown) having a hemostatic valve. Guide catheter 13 is generally constructed to bridge between a femoral artery access site and a cervical region of the carotid or vertebral artery and may be chosen according to several standard designs that are generally available. Accordingly, guide catheter 13 may be at least 85 cm long, and more particularly may be between about 95 cm and about 105 cm long. Further to conventional and available designs, inner lumen 43 of guide catheter 13 generally has an inner diameter that is between about 0.038 inch and 0.090 inch (0.88-2.29 mm), and more particularly may be between about 0.052 inch and about 0.065 inch (1.32-1.65 mm). Other designs and dimensions are contemplated.

According to embodiments, as shown in FIG. 1, retrieval catheter 13 includes, at a distal end thereof, an expandable member. For example, as shown in FIGS. 2-5, retrieval catheter 13 may include inflatable tip 50, forming a distal tip of retrieval catheter 13. Inflatable tip 50 may be disposed at least partially distal to or at least partially overlapping elongate shaft 40 of retrieval catheter 13. Inflatable tip 50 may define the distalmost end of retrieval catheter 13.

According to embodiments, as shown in FIGS. 2 and 4, inflatable tip 50 may have a first or deflated state. In the deflated state, inflatable tip 50 may have first outer cross-sectional dimension 52a, as shown in FIG. 2, and first inner cross-sectional dimension 53a, as shown in FIG. 4.

First outer cross-sectional dimension 52a and second outer cross-sectional dimension 52b may be measured as a maximum value corresponding to at least a portion of outer surface 54 in the deflated and inflated conditions, respectively. For example, first outer cross-sectional dimension 52a and second outer cross-sectional dimension 52b may be measured at or near a distal end of inflatable tip 50. First inner cross-sectional dimension 53a and second inner cross-sectional dimension 53b may be measured as a maximum value corresponding to at least a portion of inner surface 55 in the deflated and inflated conditions, respectively. For example, first inner cross-sectional dimension 53a and second inner cross-sectional dimension 53b may be measured at or near a distal end of inflatable tip 50.

According to embodiments, as shown in FIGS. 3 and 5, providing fluid from inflation lumen 56 to interior region 51 causes inflatable tip 50 to expand. For example, the introduction of fluid into interior region 51 may increase the volume of interior region 51 and cause expansion of inflatable tip 50 as pressure builds within interior region 51.

According to embodiments, as shown in FIGS. 3 and 5, inflatable tip 50 may have a second or inflated state. In the inflated state, inflatable tip 50 may have second outer cross-sectional dimension 52b, as shown in FIG. 3, and second inner cross-sectional dimension 53b, as shown in FIG. 5. Second outer cross-sectional dimension 52b may exceed first outer cross-sectional dimension 52a. Second outer cross-sectional dimension 52b may be selected and configured such that outer surface 54 (e.g., facing radially outwardly) of inflatable tip 50 engages an inner wall of a blood vessel. For example, inflatable tip 50 may be configured to limit, impede, obstruct, or prevent flow within the blood vessel past inflatable tip 50 when in the inflated state. According to embodiments, an additional inflatable member (not shown) may be provided along an outer surface of elongate body 40, proximal to inflatable tip 50. Such an additional inflatable member may be inflated to limit, impede, obstruct, or prevent flow within the blood vessel. A separate inflation lumen may be provided, or the additional inflatable member may access inflation lumen 56 connected to inflatable tip 50.

According to embodiments, second inner cross-sectional dimension 53b may exceed first inner cross-sectional dimension 53a or a cross-sectional dimension of lumen 43 of elongate body 40. Second inner cross-sectional dimension 53b may be selected and configured to receive retrieval device 11 engaged upon a thrombus. For example, as shown in FIG. 5, inner surface 55 of inflatable tip 50 forms a taper, funnel, or frustoconical shape. Inner surface 55 (e.g., facing radially inwardly) may provide a gradual transition from the blood vessel wall to lumen 43 of retrieval catheter 13, such that a thrombus brought to port 45 is guided to lumen 43, rather than around outer surface 54 of inflatable tip 50.

According to embodiments, inflatable tip 50 may have a first longitudinal length in the deflated state and a second longitudinal length in the inflated state, different from the first longitudinal length. Longitudinal lengths may be measured from a fixed point along or relative to at least a portion of delivery catheter 12. For example, a longitudinal length of inflatable tip 50 may be measured from a point or plane along elongate body 40 to a point or plane along inflatable tip 50. For example, a longitudinal length may be measured from a distal end of elongate body 40 to a distal end of inflatable tip 50. By further example, a longitudinal length may be measured from a proximal end of inflatable tip 50 to a distal end of inflatable tip 50. According to embodiments, a first longitudinal length of inflatable tip 50, in the deflated state, is less than a second longitudinal length of inflatable tip 50, in the inflated state.

According to embodiments, a distal end of inflatable tip 50 in a deflated state does not extend beyond a distal end of elongate body 40. According to embodiments, a distal end of inflatable tip 50 in an inflated state extends beyond a distal end of elongate body 40.

According to embodiments, inflatable tip 50 may be controllably inflated or deflated by a user via inflation lumen 56 in fluid communication with interior region 51 of inflatable tip 50. Inflation lumen 56 may provide fluid communication between interior portion 51 and a fluid source at or in connection with inflation port 60, as shown in FIG. 1. Inflation and deflation may be provided by a pump, a syringe, or other fluid control mechanism.

According to embodiments, inner surface 55 and outer surface 54 may be of different materials. Inner surface 55 may be of a first material and outer surface 54 may be of a second material. The first material may be more or less flexible, pliable, or compliant than the second material. For example, the first material and the second material have different modulus of elasticity. By further example, inner surface 55 may be thicker or thinner than outer surface 54. According to embodiments, one of inner surface 55 and outer surface 54 may have a smooth profile and another of inner surface 55 and outer surface 54 may have a textured profile.

According to embodiments, different features of inner surface 55 and outer surface 54 may allow inner surface 55 to be more compliant than outer surface 54. In this configuration, inflation of inflatable tip 50 causes both the inner and outer cross-sectional dimensions to increase. As inflatable tip 50 inflates, outer surface 54 expands radially outwardly. Timer surface 55 also expands radially outwardly, rather than radially inward, because inner surface 55 is more compliant than outer surface 54 and yields to the radially outward expansion of outer surface 54.

Figure 7:
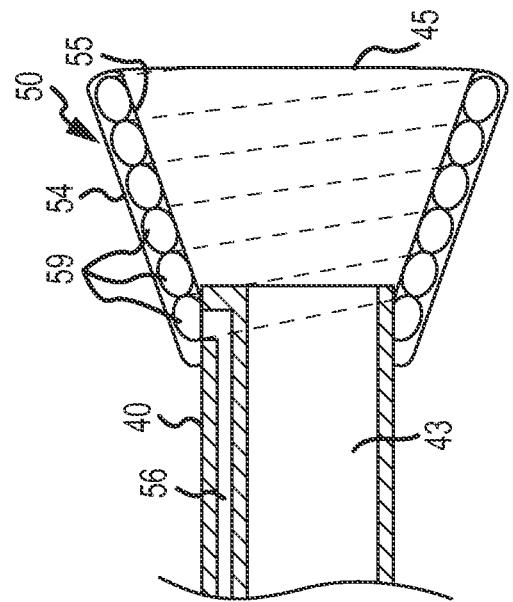
FIGS. 6 and 7 show an exemplary inflatable tip of a retrieval catheter tip having a spiral pathway, according to embodiments of the present disclosure.
Figure 6:
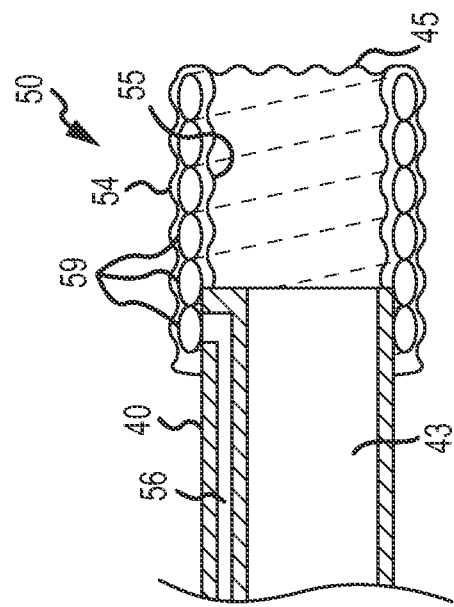

According to embodiments, as shown in FIGS. 6 and 7, fluid can be introduced within inflatable tip 50 through infusion pathway 59 between inner surface 55 and outer surface 54. Infusion pathway 59 may extend between a proximal end and a distal end of inflatable tip 50. Infusion pathway 59 may be longer than a longitudinal length of inflatable tip 50. For example, infusion pathway 59 may form a helix or spiral around a longitudinal axis of inflatable tip 50. As shown in FIGS. 6 and 7, providing fluid from inflation lumen 56 to infusion pathway 59 causes inflatable tip 50 to expand. For example, the introduction of fluid into infusion pathway 59 may increase the volume of infusion pathway 59 and cause expansion of inflatable tip 50 as pressure builds within infusion pathway 59. As shown in FIG. 7, inflatable tip 50 in an expanded state facilitates engagement with a blood vessel wall and reception of a thrombus toward lumen 43.

Suitable materials for inflatable tip 50 include biocompatible polymers. Materials for inflatable tip 50 or coatings thereon may include hydrophilic, hydrophobic, and anti-thrombogenic components. For example, inflatable tip 50 may be of silicone, polyurethane, polytetrafluoroethylene, another polymer, or combinations thereof.

Figure 9:
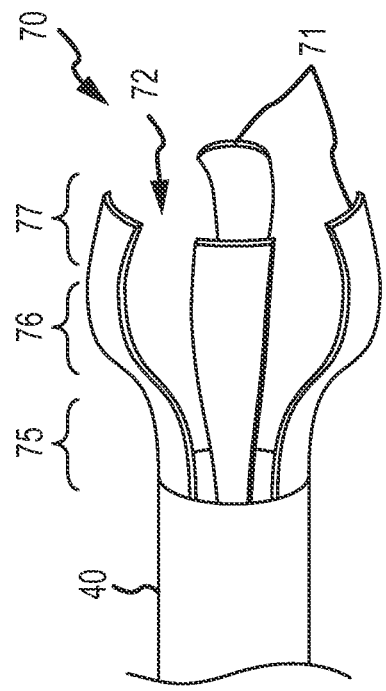
FIGS. 8 and 9 show an exemplary expandable retrieval catheter tip, according to embodiments of the present disclosure.
Figure 8:
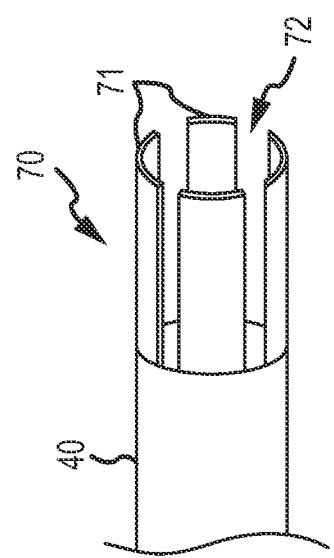

According to embodiments, as shown in FIGS. 8 and 9, expandable tip 70 may include a plurality of strips 71 extending from elongate body 40. As shown in FIG. 8, each of the plurality of strips 71 may extend longitudinally from elongate body 40 in a first state. Each of the plurality of strips 71 may be circumferentially adjacent to another of the plurality of strips 71. A longitudinally-extending slit 72 may be disposed between circumferentially adjacent pairs of strips 71. Expandable tips 70 may include any number of strips 71 (e.g., one or more strips).

According to embodiments, as shown in FIG. 8, expandable tip 70 may have a first or unexpanded state. According to embodiments, as shown in FIG. 9, expandable tip 70 may have a second or expanded state. In the expanded state, at least a portion of expandable tip 70 may have a cross-sectional dimension greater than the cross-sectional dimension of the at least a portion in the unexpanded state.

According to embodiments, as shown in FIG. 9, expandable tip 70, or other expandable devices or components disclosed herein (e.g., expandable tip 80, expandable tip 90, etc.), may include first portion 75, second portion 76, and third portion 77. In the expanded state, first portion 75 may have a cross-sectional dimension greater than or less than a cross-sectional dimension of either or each of second portion 76 and third portion 77. In the expanded state, second portion 76 may have a cross-sectional dimension greater than or less than a cross-sectional dimension of either or each of first portion 75 and third portion 77. In the expanded state, third portion 77 may have a cross-sectional dimension greater than or less than a cross-sectional dimension of either or each of first portion 75 and second portion 76.

For example, a first portion 75 may be located adjacent to elongate body 40. In the expanded state, expandable tip 70 may gradually taper from a first cross-sectional dimension at first portion 75 to a second cross-sectional dimension, greater than the first cross-sectional dimension, at second portion 76, distal to first portion 75. Providing second portion 76 with greater cross-sectional dimension than first portion 75 provides a smooth transition into a lumen within the elongate body 40. Expandable tip 70 may further taper to a third cross-sectional dimension, less than the second cross-sectional dimension, at third portion 77, distal to second portion 76. Providing third portion 77 with smaller cross-sectional dimension than second portion 76 provides a relatively atraumatic distal end of expandable tip 70.

According to embodiments, as shown in FIGS. 8 and 9, expandable tip 70 transitions from and unexpanded state to an expanded state. According to embodiments, this transition may occur upon entry of a retrieval device and/or a thrombus into expandable tip 70. The retrieval device and/or thrombus, or a portion thereof, may have an outer diameter that is greater than the inner diameter of the expandable tip 70 in the unexpanded state. Expandable tip 70 may be of a flexible material, such that the retrieval device and/or thrombus pushes expandable tip 70 open and causes it to expand radially.

Figure 11:
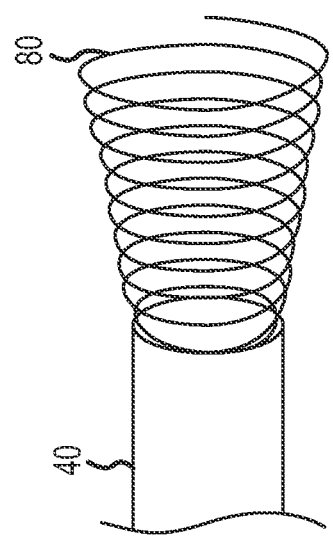
FIGS. 10 and 11 show an exemplary expandable retrieval catheter tip, according to embodiments of the present disclosure.
Figure 10:
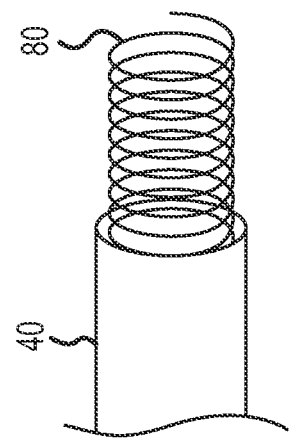

According to embodiments, as shown in FIGS. 10 and 11, expandable tip 80 may include a helically wound coil extending from elongate body 40. Expandable tip 80 may form a lumen extending there through and connecting with the lumen of elongate body 40. According to embodiments, as shown in FIG. 10, expandable tip 80 may have a first or unexpanded state. According to embodiments, as shown in FIG. 11, expandable tip 80 may have a second or expanded state. In the expanded state, at least a portion of expandable tip 80 may have a cross-sectional dimension greater than the cross-sectional dimension of the at least a portion in the unexpanded state.

According to embodiments, as shown in FIG. 11, expandable tip 80 in an expanded state may provide a variable inner cross-sectional dimension. For example, a first inner cross-sectional dimension, at a proximal end of expandable tip 80, may be less than a second inner cross-sectional dimension, at a distal end of expandable tip 80. Expandable tip 80 may provide a transition from a cross-sectional dimension of a vessel lumen to a cross-sectional dimension of elongate body 40.

According to embodiments, expandable tip 80 may maintain or alter its longitudinal length as it transitions from and unexpanded state to an expanded state. According to embodiments, expandable tip 80 may maintain or alter its pitch (angle of winding relative to a longitudinal axis) as it transitions from and unexpanded state to an expanded state. In either or both of the unexpanded state and the expanded state, expandable tip 80 may have a closed pitch, wherein longitudinally adjacent windings of the helical coil contact each other. In either or both of the unexpanded state and the expanded state, expandable tip 80 may have an open pitch, wherein longitudinally adjacent windings of the helical coil are separated by an open space.

According to embodiments, as shown in FIGS. 10 and 11, expandable tip 80 transitions from and unexpanded state to an expanded state. According to embodiments, this transition may occur upon entry of a retrieval device and/or a thrombus into expandable tip 80. The retrieval device and/or thrombus, or a portion thereof, may have an outer diameter that is greater than the inner diameter of the expandable tip 80 in the unexpanded state. Expandable tip 80 may be of a flexible material, such that the retrieval device and/or thrombus pushes expandable tip 80 open and causes it to expand radially.

According to embodiments, as shown in FIGS. 12-15, woven expandable tip 90 may be a stent-like structure made of two or more round, ovoid, or rectangular wire filaments. The filaments may be formed of known flexible materials including shape memory materials, such as nitinol, platinum and stainless steel. According to embodiments, expandable tip 90 is fabricated from platinum/8% tungsten and 35N LT (cobalt nickel alloy, which is a low titanium version of MP35N alloy) alloy wires. According to embodiments, one or more of the filaments can be formed of a biocompatible metal material or a biocompatible polymer, such as silicone or polyurethane.

According to embodiments, the wire filaments of expandable tip 90 may be woven into a lattice-like structure by providing helical windings in opposite directions (i.e., dextrorotary and levorotary). In at least one embodiment, during braiding or winding of the expandable tip 90, the filaments may be loosely braided using a 1-over-2-under-2 system. The filaments may be unfixed at crossing points, such that they may slide relative to each other. In other embodiments, however, other methods of braiding may be followed, without departing from the scope of the disclosure. At least some of the filament ends of the expandable tip 90 may be cut to length and therefore remain free for radial expansion and contraction. Expandable tip 90 may exhibit a high degree of flexibility due to the materials used, the density (or porosity) of the filaments, and ends being unfixed, at least at one end. Strands at a proximal end of expandable tip 90 may be attached to a distal end of elongate body 40.

According to embodiments, as shown in FIGS. 12-15, expandable tip 90 transitions from and unexpanded state to an expanded state. According to embodiments, this transition may occur upon entry of a retrieval device and/or a thrombus into expandable tip 90. The retrieval device and/or thrombus, or a portion thereof, may have an outer diameter that is greater than the inner diameter of the expandable tip 90 in the unexpanded state. Expandable tip 90 may be of a flexible material, such that the retrieval device and/or thrombus pushes expandable tip 90 open and causes it to expand radially.

Figure 12:
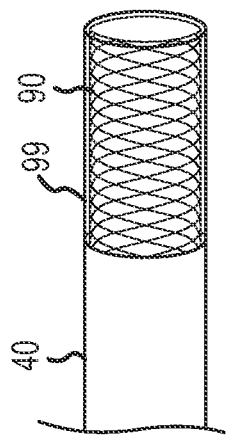
FIG. 12 shows an exemplary woven retrieval catheter tip with removable covering, according to embodiments of the present disclosure.

According to embodiments, expandable tip 90 may be self-expanding, such that expandable tip 90 may transition to an expanded state when unrestrained. According to embodiments, as shown in FIG. 12, expandable tip 90 may be provided with cover 99 about an outer surface thereof. Cover 99 may be provided along an entire length of expandable tip 90 or a portion thereof. When in place over expandable tip 90, cover 99 may provide a radially constraining force that maintains expandable tip 90 in an unexpanded state. For example, cover 99 may span a fully circumferential distance about expandable tip 90.

Figure 13:
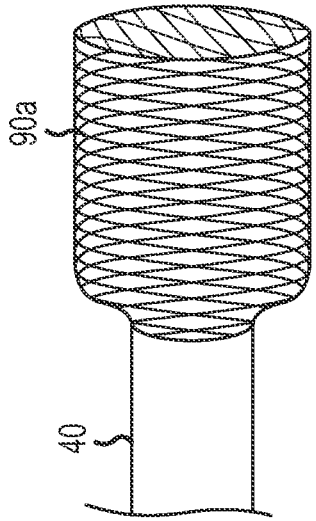
FIGS. 13, 14, and 15 show exemplary woven retrieval catheter tips, according to embodiments of the present disclosure.
Figure 15:
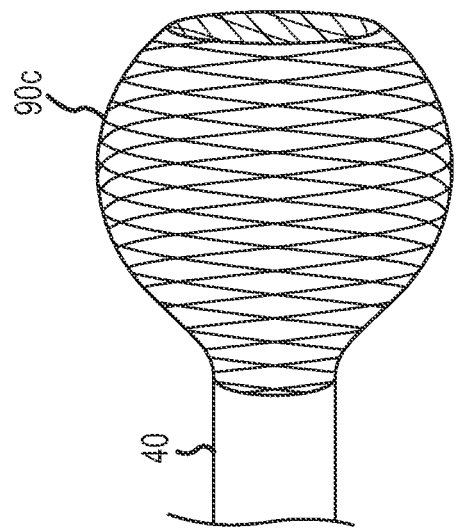
Figure 14:
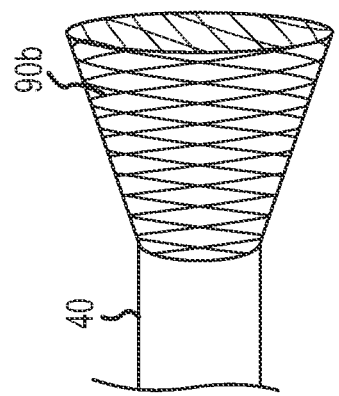

Removal of cover 99 may allow expandable tip 90 to transition to an expanded state. According to embodiments, as shown in FIGS. 13-15, expandable tip 90 may be provided with one of a plurality of shapes in an expanded state. An expanded shape of expandable tip 90 may be predetermined by a process such as heat setting, wherein expandable tip 90 is annealed while faulted in its expanded shape. Subsequent to this process, expandable tip 90 may be constrained in an unexpanded shape, for example, by cover 99. For example, as shown in FIG. 13, expandable tip 90$a$ may extend from elongate body 40 and expand to a substantially cylindrical shape along at least a portion thereof. By further example, as shown in FIG. 14, expandable tip 90$b$ may extend from elongate body 40 and form a substantially frustoconical shape. By further example, as shown in FIG. 15, expandable tip 90$c$ may extend from elongate body and reach a maximum cross-sectional dimension at other than a distalmost end of expandable tip 90. From a location of a maximum cross-sectional dimension, expandable tip 90 may further extend distally by tapering radially inwardly approaching the distalmost end of expandable tip 90. As will be appreciated by those having skill in the art, the various embodiments and aspects thereof illustrated and described herein are combinable to form any number of devices. For example, cover 99 may be provided on inflatable tip 50 or expandable tip 70, 80, or 90.

According to embodiments, cover 99 may be of a material that is water-soluble. For example, cover 99 may be dissolved when exposed to a fluid, such as water or blood. For example, materials may include polyvinyl alcohol, polyvinyl pyrrolidon, poly(ethylene glycol), polyacrylic acid (PAA), polyacrylamide, N-(2-hydroxypropyl) methacrylamide (HPMA), divinyl ether-maleic anhydride (DIVEMA), poly(2-alkyl-2-oxazolines), polyphosphates, polyphosphazene, xanthan gum, pectins, chitin, chitosan, dextran, carrageenan, guar gum, cellulose ethers, sodium CMC, hyaluronic acid, albumin, starch, or combinations thereof. Upon delivery of retrieval catheter 13 and in preparation for reception of a thrombus, expandable tip 90 may be exposed to blood within a blood vessel, whereby cover 99, or portion thereof, is dissolved and removed from at least a portion of expandable tip 90. A span of time allowing cover 99, or a portion thereof, to dissolve may be based upon properties of the material or a thickness of cover 99. The span of time required may be pre-selected to correspond to a span of time for delivering retrieval catheter 13 and engaging a thrombus with retrieval device 11.

According to embodiments, cover 99 may be of a material that is configured to dissolve, separate, or remove upon exposure to an input comprising at least one of light, heat, and an electric field. Exposure to an input may cause at least a portion of cover 99 to be removed from expandable tip 90.

According to embodiments, cover 99 may be provided to any one or more of the components disclosed herein, including inflatable tip 50 or expandable tip 70, 80, or 90.

According to embodiments, suitable materials for expandable tip 70, 80, or 90 include biocompatible polymers. For example, materials may include silicone, polyurethane, polytetrafluoroethylene, another polymer, or combinations thereof. According to embodiments, suitable materials include shape memory polymers. According to embodiments, expandable tip 70, 80, or 90 may react to an input or when activated. As used herein, "input" refers to an action taken by a user with respect to the environment of a portion of the system. An input may include induced electric fields, magnetic fields, pressure conditions, light (e.g., ultraviolet light), heat, biological conditions, or chemical conditions.

The input may activate, or cause or contribute to a response, the relevant portion of the system. As used herein, "response" refers to changes in material dimensions/size, secondary structure, solubility, or degree of intermolecular association of a portion of the system. The input may induce formation or destruction of secondary forces (hydrogen bonding, hydrophobic effects, electrostatic interactions, etc.), simple reactions (e.g., acid-base reactions) of moieties pendant to a polymer backbone, and/or osmotic pressure differentials that result from such phenomena.

According to embodiments, materials for expandable tip 70, 80, or 90 may include an electro-active or electro-responsive polymer. Electronic electro-active polymers may be actuated by application of an electrical field. Some examples of electronic electro-active polymers include dielectric electro-active polymers, electro-strictive graft elastomers, electro-strictive paper, electro-viscoelastic elastomers, and ferroelectric polymers. Ionic electro-active polymers may be actuated by induced mobility or diffusion of ions. Some examples of ionic electro-active polymers carbon nanotubes, conductive polymers, electro-rheological fluids, ionic polymer gels, and ionic polymer metallic composites. Electro-responsive polymers may include, without limitation, chitosan, chondroitin sulfate, hyaluronic acid, alginate, vinyl alcohol, allylamine, acrylonitrile, 2-acrylamido-2-methylpropane sulfonic acid, aniline, polyhydroxyethylmethacrylate, methacrylic acid, acrylic acid, vinyl sulfonic acids, or combinations thereof. Retrieval catheter 13 may be provided with a voltage source at a proximal end thereof and at least one lead at a distal end thereof, in selectable electrical conduction with the voltage source. Upon delivery of retrieval catheter 13 and in preparation for reception of a thrombus, a user may activate a switch to allow electrical power to be provided from the voltage source to the lead. The lead may conduct electricity directly to the expandable tip or to a vicinity of the expandable tip, thereby inducing the expandable tip to transition to an expanded state. Alternatively, electricity provided directly to the expandable tip or to a vicinity of the expandable tip may induce the expandable tip to transition to an unexpanded state.

According to embodiments, materials for expandable tip 70, 80, or 90 may include a photo-responsive polymer. A photo-responsive polymer may be actuated by visible light, ultraviolet light, or other wavelengths of the electromagnetic spectrum. Photo-responsive polymers may include, without limitation, azobenzene-containing block copolymers, poly(Nhydroxy propyl methacrylamide) (PHPMA), polyacrylic acid (PAA), poly(2-(dimethylamino)ethyl methacrylate) (PDMAEMA), poly(N-isopropylacrylamide) (PNIPAM), or combinations thereof. Retrieval catheter 13 may be provided with a light source at a proximal end thereof and at least one optical fiber or other light-conducting member at a distal end thereof, in connection with the light source. Upon delivery of retrieval catheter 13 and in preparation for reception of a thrombus, a user may activate a switch to allow light to be provided from the light source to the optical fiber. The optical fiber may provide light directly to the expandable tip or to a vicinity of the expandable tip, thereby inducing the expandable tip to transition to an expanded state. Alternatively, light provided directly to the expandable tip or to a vicinity of the expandable tip may induce the expandable tip to transition to an unexpanded state.

According to embodiments, materials for expandable tip 70, 80, or 90 may include a thermally-responsive polymer or alloy. Thermally-responsive polymers may include, without limitation, acrylonitrile butadiene styrene (ABS), acrylic-based polymers such as PMMA, celluloid, cellulose acetate, cyclic olefin copolymer (COC), ethylene-vinyl acetate (EVA), ethylene vinyl alcohol (EVOH), fluoroplastics, such as PTFE, FEP, PFA, CTFE, ECTFE, and ETFE, ionomers, KYDEX™, an acrylic/polyvinyl chloride (PVC) alloy, liquid crystal polymer (LCP), polyoxymethylene (POM or acetal), polyacrylates, polyacrylonitrile (PAN or acrylonitrile), polyamide (PA or Nylon), polyamide-imide (PAI), polyaryletherketone (PAEK or Ketone), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), chlorinated polyethylene (CPE), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC), ptyrene-acrylonitrile (SAN), or combinations thereof. A thermally-responsive polymer may be actuated by an increase in ambience temperature (e.g., the material having a transition temperature of about 30° C.). Upon delivery of retrieval catheter 13 and in preparation for reception of a thrombus, a user may expose the expandable tip to an ambient environment at or above a transition temperature. As the expandable tip reaches equilibrium with the ambient environment and crosses the transition temperature, the expandable tip is induced to transition to an expanded state. Alternatively, heat may induce the expandable tip to transition to an unexpanded state.

According to embodiments, the cover 99 may be removed from the expandable tip 70, 80, or 90. For example, the cover 99 may be retracted proximally to unsheathe the expandable tip 70, 80, or 90. Removal or retraction of the cover 99 may be performed with a mechanism extending within a lumen of the guide catheter 13 or the delivery catheter 12. This mechanism may be controlled by a user at a proximal end of the guide catheter 13. According to embodiments, two or more shafts may extend an entire length of the catheter 13. One of the shafts (e.g., an outer shaft) may cover the expandable tip 70, 80, or 90, and another of the shafts (e.g., an inner shaft) may connect to the expandable tip 70, 80, or 90. The outer shaft may be retrieved proximally and/or the inner shaft may be pushed distally. Accordingly, the cover 99 may be retracted relative to the expandable tip 70, 80, or 90. According to embodiments, retraction of the cover 99 may be executed before or after one or more of the inputs disclosed herein.

More specific features of the use of the device and system of the disclosure in capturing and removing objects, such as thromboembolic occlusions, from vessels, such as distal cerebral vessels, are described below, with reference to FIGS. 16-21. Description of methods and procedures disclosed herein is applicable to any of the devices and systems disclosed herein.

According to embodiments, an access site is prepared as either a puncture wound or as a surgical cut-down, such as in the femoral artery or at other peripheral vessels such as a brachial artery. A conventional introducer (not shown) may be used to provide hemostatic access at the access site via an incorporated hemostatic valve. Guide catheter 13 is then advanced through the introducer until distal end 42 is positioned with distal port 45 at a region of a cervical vessel, thereby providing transluminal access to the cervical vascular tree.

According to embodiments, as shown in FIG. 16, delivery catheter 12 is advanced through the inner lumen 43 of guide catheter 13 and out the distal port 45 thereof until the distal end 34 of the delivery catheter is positioned within vessel 102 adjacent to object 100, as shown in FIG. 16, or beyond object 100, as shown in FIG. 17. Retrieval catheter 13 may remain at a location proximal to object 100. According to embodiments, delivery catheter 12 may be advanced over a conventional guide wire (not shown), such as in the case where the location of object 100 is beyond a bifurcated vessel or otherwise tortuous cerebral vessels. Once the delivery catheter 12 is positioned adjacent to or beyond object 100, the guide wire is removed from the patient and is then replaced with retrieval device 11.

According to embodiments, from the embodiment shown in FIG. 16, retrieval device 11 may be advanced distally through inner lumen 36 of delivery catheter 12 until it exits through distal port 35 into the blood vessel where the engaging portion 17 engages object 100.

According to embodiments, from the embodiment shown in FIG. 17, delivery catheter 12 is withdrawn, while retrieval device 11 remains in its location relative to object 100, whereby retrieval device 11 is unsheathed. Unsheathing retrieval device 11 allows retrieval device 11 to engage the object 100, such as by expanding into object 100, as shown in FIG. 18.

Figure 19:
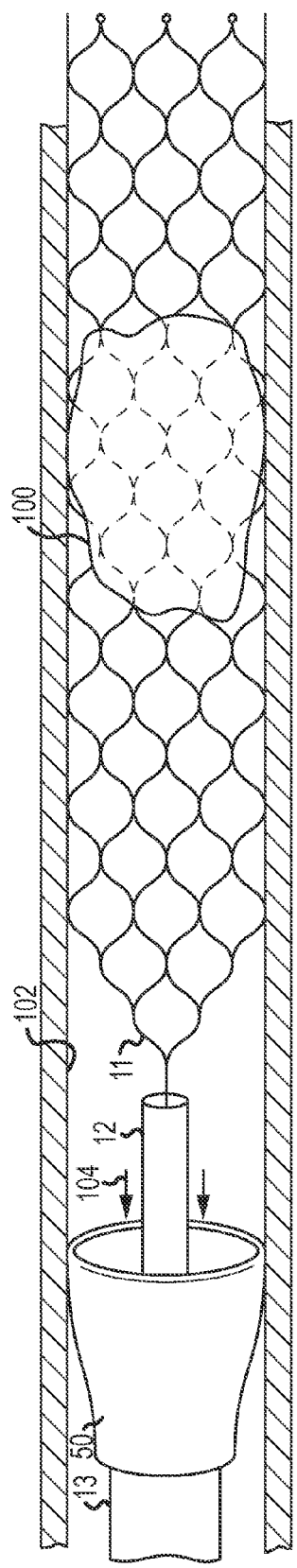
FIG. 19 shows a step of an exemplary method, wherein an inflatable tip is inflated, according to embodiments of the present disclosure.

According to embodiments, as shown in FIG. 19, inflatable tip 50 of retrieval catheter 13 may be expanded or inflated prior to receiving object 100. According to embodiments, as shown in FIG. 19, inflatable tip 50 may expand to have an outer cross-sectional dimension configured to engage walls of blood vessel 102. According to embodiments, as shown in FIG. 19, inflatable tip 50 may expand to have an inner cross-sectional dimension configured to receive object 100. It will be understood by those having ordinary skill in the art that steps relating to inflatable tip 50 may also be applied to expandable tip 70, 80, or 90 or any other device disclosed herein for retrieval of object 100. Such elements may transition from an unexpanded state to an expanded state as disclosed herein prior to receiving object 100.

According to embodiments, inflatable tip 50 may impede or prevent flow within blood vessel 102 from a proximal side of inflatable tip 50 to a distal side of inflatable tip 50. As shown in FIG. 19, aspiration may be provided to create flow 104 from a location distal to inflatable tip 52 within inner lumen 43. Flow 104 facilitates retrieval and capture of object 100 and portions thereof that may break free of retrieval device 11 during the disclosed procedure. With aspiration, such portions are drawn to within the inner lumen 43, rather than embolizing to a location distal to retrieval system 10.

Figure 20:
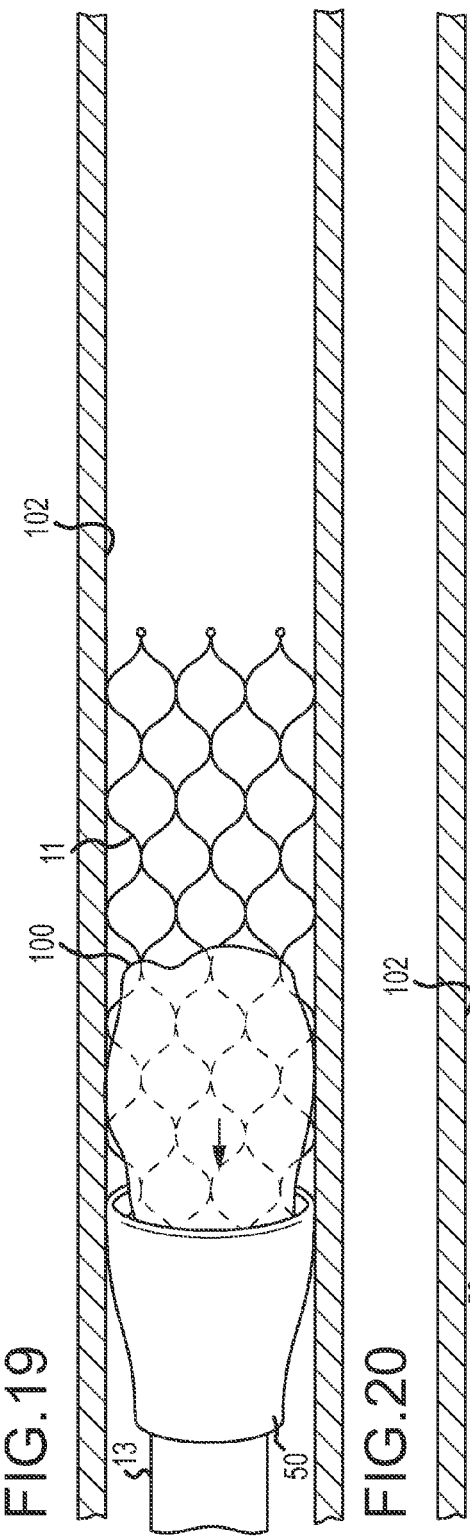
FIG. 20 shows a step of an exemplary method, wherein the thrombus is captured within the inflatable tip, according to embodiments of the present disclosure.

According to embodiments, as shown in FIG. 20, retrieval device 11 engaged with object 100 is received within inflatable tip 50 and inner lumen 43 of retrieval catheter 13.

Figure 21:
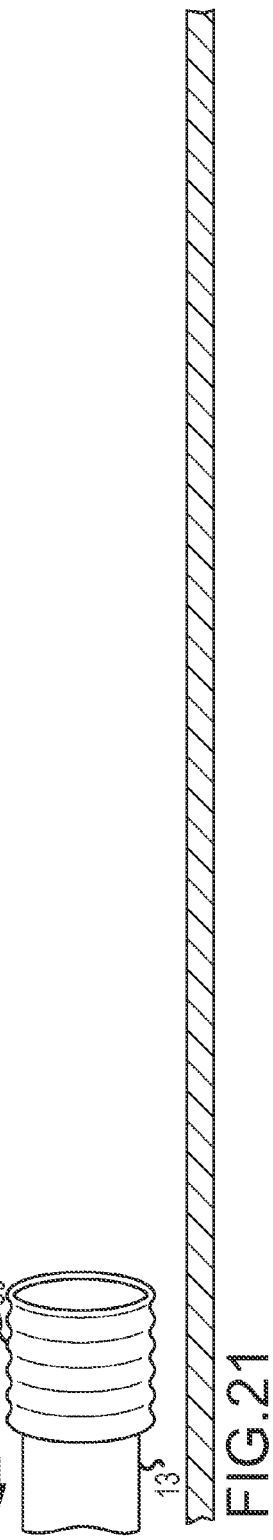
FIG. 21 shows a step of an exemplary method, wherein the inflatable tip is deflated, according to embodiments of the present disclosure.

According to embodiments, as shown in FIG. 21, inflatable tip 50 may be deflated to provide a decreased outer cross-sectional dimension. Retrieval catheter 13 and other components of retrieval system 10 may be withdrawn proximally. Retrieval device 11, delivery catheter 12, and object 100 may be removed from the location and further from the body, either through retrieval catheter 13 or together in combination with retrieval catheter 13.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, and C" includes at least one of only A, of only B, of only C, of any combination of A, B, and C; and/or of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A retrieval catheter, comprising:
    an elongate shaft having a shaft lumen extending from a proximal end portion to a distal end portion of the elongate shaft;
    an inflatable tip disposed at a distal end of the elongate shaft, the inflatable tip extending distally of the distal end and having an outer surface and an inner surface forming a tip lumen distally of the distal end;
    wherein, in an expanded state, the inner surface is expanded radially outwardly relative to the inner surface in an unexpanded state;
    wherein, in the unexpanded state, the inner surface is smoother than the outer surface and the outer surface is more textured than the inner surface;
    wherein the inflatable tip comprises a spiral pathway between the inner surface and the outer surface and extending between a proximal end of the inflatable tip and a distal end of the inflatable tip; and
    wherein (i) an entire length of the inner surface between the proximal end of the inflatable tip and the distal end of the inflatable tip and (ii) an entire length of the outer surface between the proximal end of the inflatable tip and the distal end of the inflatable tip are radially separated by the spiral pathway.

2. The catheter of claim 1, wherein, in the unexpanded state, the inflatable tip has a cylindrical profile.

3. The catheter of claim 1, wherein, in the expanded state, the inflatable tip has a frusticonical profile.

4. The catheter of claim 1, wherein the inner surface is more compliant than the outer surface.

5. The catheter of claim 1, wherein, in the expanded state, the inflatable tip has a greater volume than in the unexpanded state.

6. The catheter of claim 1, wherein in the unexpanded state, the inflatable tip has a first maximum outer cross-sectional dimension and wherein, in the expanded state, the inflatable tip has a second maximum outer cross-sectional dimension greater than the first maximum outer cross-sectional dimension.

7. The catheter of claim 1, wherein the inflatable tip is in fluid communication with a fluid source.

8. The catheter of claim 7, further comprising a pump configured to controllably move fluid between the inflatable tip and the fluid source.

9. The catheter of claim 1, wherein the inflatable tip extends a greater longitudinal distance in the expanded state than in the unexpanded state.

10. The catheter of claim 1, wherein the inner surface is thicker than the outer surface.

11. The catheter of claim 1, wherein the inner surface is of a first material having a first modulus of elasticity and the outer surface is of a second material having a second modulus of elasticity, different from the first modulus of elasticity.

12. The catheter of claim 1, wherein, in the expanded state, the inner surface is not expanded radially inwardly relative to the inner surface in the unexpanded state.

13. A method of treating a blood vessel, comprising:
    advancing an elongate shaft within the vessel to a location adjacent an object within the vessel, the elongate shaft having a shaft lumen extending from a proximal end portion to a distal end portion of the elongate shaft;
    inflating an inflatable tip disposed at a distal end of the elongate shaft and extending distally of the distal end with an outer surface and an inner surface to form a tip lumen distally of the distal end, the inflatable tip transitioning from an unexpanded state to an expanded state, such that the inner surface is expanded radially outwardly relative to the inner surface in the unexpanded state, wherein, in the unexpanded state, the inner surface is smoother than the outer surface and the outer surface is more textured than the inner surface, wherein the inflatable tip comprises a spiral pathway between the inner surface and the outer surface and extending, in the expanded state, between a proximal end of the inflatable tip and a distal end of the inflatable tip, wherein (i) an entire length of the inner surface between the proximal end of the inflatable tip and the distal end of the inflatable tip and (ii) an entire length of the outer surface between the proximal end of the inflatable tip and the distal end of the inflatable tip are radially separated by the spiral pathway; and
    receiving the object into the shaft lumen through the tip lumen.

14. The method of claim 13, wherein inflating the inflatable tip comprises moving fluid from a fluid source to an interior region of the inflatable tip.

15. The method of claim 13, whereby the inner surface and the outer surface of the inflatable tip expand radially outward.

16. The method of claim 13, wherein receiving the object comprises providing suction at the distal end of the elongate shaft.

17. The method of claim 13, wherein the inner surface is thicker than the outer surface.

18. The method of claim 13, wherein the inner surface is of a first material having a first modulus of elasticity and the outer surface is of a second material having a second modulus of elasticity, different from the first modulus of elasticity.

19. The method of claim 13, wherein the inner surface is not expanded radially inwardly when transitioning from the unexpanded state to the expanded state.

* * * * *